United States Patent
Nicolaas (10) Patent No.: US 11,107,582 B2
(45) Date of Patent: Aug. 31, 2021

(54) GUIDELINE-BASED DECISION SUPPORT

(71) Applicant: KONINKLIJKE PHILIPS N.V., Eindhoven (NL)

(72) Inventor: Arvid Randal Nicolaas, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 996 days.

(21) Appl. No.: 14/423,578

(22) PCT Filed: Sep. 3, 2013

(86) PCT No.: PCT/IB2013/058246
§ 371 (c)(1),
(2) Date: Feb. 24, 2015

(87) PCT Pub. No.: WO2014/037872
PCT Pub. Date: Mar. 13, 2014

(65) Prior Publication Data
US 2015/0227701 A1    Aug. 13, 2015

Related U.S. Application Data

(60) Provisional application No. 61/697,322, filed on Sep. 6, 2012.

(51) Int. Cl.
*G16H 50/20* (2018.01)
*G16H 70/60* (2018.01)
*G06N 20/00* (2019.01)

(52) U.S. Cl.
CPC ............ *G16H 50/20* (2018.01); *G06N 20/00* (2019.01); *G16H 70/60* (2018.01)

(58) Field of Classification Search
None
See application file for complete search history.

(56) References Cited

U.S. PATENT DOCUMENTS 5,583,758 A * 12/1996 McIlroy ............... G06F 19/325
705/2
5,644,686 A * 7/1997 Hekmatpour ......... G06F 3/0481
706/45

(Continued)

FOREIGN PATENT DOCUMENTS

EP       1089222 A1   4/2001
WO    2014037872 A2   3/2014

OTHER PUBLICATIONS

Tu, Samson W et al. "The structure of guideline recommendations: a synthesis." AMIA . . . Annual Symposium proceedings. AMIA Symposium vol. 2003 (2003): 679-83. (Year: 2003).*

(Continued)

*Primary Examiner* — Rachel L. Porter (57) ABSTRACT

A system for decision support comprises a path unit (10) for determining a determined path through a decision tree (2) that leads to a determined recommendation node (4) comprising a determined recommendation. The decision tree (2) comprises condition nodes (3) and recommendation nodes (4), wherein a condition node (3) comprises a condition associated with a particular branch of the decision tree (2). A recommendation node (4) comprises a recommendation associated with the one or more conditions of the one or more condition nodes (3) on a path towards the recommendation node (4). The path unit (10) is arranged for taking into account the conditions of the condition nodes (3) along the path by applying the conditions to a set of parameters (1). The system comprises an explanation unit (11) for generating an explanation of a reason for the determined recommendation based on at least one of the condition nodes (3) on the path that leads to the recommendation node (4).

11 Claims, 8 Drawing Sheets

(56) References Cited

U.S. PATENT DOCUMENTS

| | | | | |
|---|---|---|---|---|
| 7,162,464 | B1 | 1/2007 | Miller et al. | |
| 7,877,272 | B2* | 1/2011 | Rosales | G16H 20/00 705/2 |
| 2002/0002325 | A1* | 1/2002 | Iliff | G06Q 50/22 600/300 |
| 2004/0044546 | A1* | 3/2004 | Moore | G06F 19/325 705/2 |
| 2005/0256961 | A1* | 11/2005 | Alon | H04L 29/06 709/229 |
| 2010/0088320 | A1* | 4/2010 | Fortier | G06Q 50/24 707/746 |

OTHER PUBLICATIONS

Bellazzi, R. et al. "Predictive data mining in clinical medicine: Current issues and guidelines", International Journal of Medical Informatics, Feb. 2008; 77(2):81-97.

Moskovitch, R. et al. "Multiple Hierarchical Classification of a Free-Text Clinical Guidelines", Artif Intell Med. Jul. 2006; 37(3):177-90.

Krahn, M.D. et al. "Primer on Medical decision Analysis: Part 4—Analyzing the Model and Interpreting the Results", Med Decis Making. Apr.-Jun. 1997; 17(2):142-51.

Laeson, R.C., (2000) "Knowledge Representation of Situation-Specific Clinical Practice Guidelines", (Doctoral dissertation, Harvard Medical School).

Shortliffe, E.H., (1979) "Knowledge Engineering for Medical Decision Making: a Review of Computer-Based Clinical Decision Aids", proceedings of the IEEE, 67(9), 1207-1224.

Aguirre-Junco, A-R et al: "Computerization of guidelines: a knowledge specification method to convert text to detailed decision tree for electronic implementation", Studies in Health Technology and Informatics, IOS Press, Amsterdam, NL, vol. 107, 2004, pp. 115-119.

Samson W Tu et al: "The structure of guideline recommendations: a synthesis", AMIA Annual Symposium proceedings, 2003, pp. 679-683, U.S.

Samson, W. Tu et al: "The SAGE Guideline Model: Achievements and Overview", Journal of the American Medical Informatics Association (JAMIA), vol. 14, No. 5 Sep.-Oct. 2007, pp. 589-598.

Wang, Dongwen et al "Design and Implementation of the GLIFs Guideline Execution Engine", Journal of Biomedical Informatics, vol. 37, 2004, pp. 305-318.

\* cited by examiner

GUIDELINE-BASED DECISION SUPPORT

CROSS-REFERENCE TO PRIOR APPLICATIONS

This application is the U.S. National Phase application under 35 U.S.C. § 371 of International Application No. PCT/IB2013/058246, filed on Sep. 3, 2013, which claims the benefit of U.S. Provisional Application No. 61/697,322, filed on Sep. 6, 2012. These applications are hereby incorporated by reference herein.

FIELD OF THE INVENTION

The invention relates to decision support. The invention further relates to decision support based on a decision tree.

BACKGROUND OF THE INVENTION

Clinical guidelines may comprise evidence-based documents that evaluate results from clinical studies and provide recommendations for treatment of patients with certain characteristics and disease profiles. Increasingly, governments enforce the usage of guidelines in clinical practice to prevent malpractice and standardize care throughout the countries.

Clinical pathways describe the workflow that a patient goes through in a hospital. These pathways are usually based on a guideline. Guidelines describe which treatment may give the best outcome given a particular set of conditions, whereas pathways describe a sequence of steps that are performed in respect of a patient. The known efforts to formalize guidelines do not make a distinction between the concepts of guidelines and pathways. Consequently, known decision support algorithms need input information on the past history of the patient. Usually, it is quite difficult to compile a structured history list containing all necessary information.

One of the aims in healthcare informatics is to bring knowledge from clinical guidelines to the point of care. The knowledge embedded in the clinical guidelines may be used as a source of information to provide Clinical Decision Support (CDS), such that recommendations can be given based on that knowledge, and warnings can be issued upon deviation from the guidelines.

"Predictive data mining in clinical medicine: Current issues and guidelines", by Riccardo Bellazzi and Blaz Zupan, in: International Journal of Medical Informatics Volume 77, Issue 2, Pages 81-97, February 2008, discloses methods of predictive data mining in clinical medicine with the goal to derive models that can use patient specific information to predict the outcome of interest and to thereby support clinical decision-making. Classification with a decision tree means following a path from the root node to the leaf, which also determines the outcome and its probability. In addition, each path in the decision tree can be regarded as a decision rule.

SUMMARY OF THE INVENTION

It would be advantageous to have improved decision support. To better address this concern, a first aspect of the invention provides a system comprising a path unit for determining a determined path through a decision tree that leads to a determined recommendation node comprising a determined recommendation, wherein the decision tree comprises condition nodes and recommendation nodes, wherein a condition node comprises a condition associated with a particular branch of the decision tree, and wherein a recommendation node comprises a recommendation associated with one or more conditions of one or more condition nodes on a path towards the recommendation node, and wherein the path unit is arranged for taking into account the conditions of the condition nodes on the path by evaluating the conditions based on a set of parameters; and an explanation unit for generating an explanation of a reason for the determined recommendation based on at least one of the condition nodes on the path that leads to the recommendation node.

By evaluating the conditions of the decision tree's condition nodes in view of a set of parameters, the decision tree allows to make a decision based on the set of parameters, and does not need to model the history involved in the patient pathway, if this information is not necessary to make a decision. By providing an explanation of the reason for the recommendation, based on at least one of the condition nodes on the path that leads to the recommendation node, the user may be informed of why this recommendation is given. This may improve the trust of the user in the system, and/or may allow the user to override the recommended course of action in case the reasons for giving the recommendation are not convincing.

The path unit may be arranged for determining the determined path through the decision tree from a root node to the determined recommendation node. By starting from a predetermined root node, the algorithm can provide the path more easily.

The condition node may comprise a condition that determines whether the path is allowed to intersect the condition node. This provides a flexible way of modeling the guideline as a decision tree. For example, the condition is a Boolean expression that determines whether the path may pass that condition node towards a recommendation node, or whether another path not intersecting that condition node should be determined.

The path unit may be arranged for identifying a plurality of paths leading to a plurality of corresponding recommendation nodes, taking into account the conditions of the condition nodes on the plurality of paths. This way, a plurality of recommendations of a plurality of different recommendation nodes may be applicable based on a given set of parameters. This may be the case if several condition nodes have conditions that allow the path to intersect those latter condition nodes.

The system may comprise a report unit for enabling a user to create a report. The system may further comprise a parameter unit for determining the set of parameters based on information in the report and/or information in an information record. The user does not have to change her normal working behavior, because she can create the report without having to provide information to the decision support system separately. Moreover, the set of parameters, and the determined path and determined recommendation node may be updated as the report is being written, to enable the system to pro-actively inform the user of a determined recommendation.

The system may further comprise a presence unit for indicating the presence of an applicable recommendation to the user. The system may further comprise a recommendation request unit for enabling a user to provide an indication of a request. The system may further comprise a recommendation display unit for displaying the determined recommendation to the user in response to the request. This further reduces interruption of the user during her work. By merely indicating the presence of a determined recommendation, and displaying the recommendation itself to the user only after the user requests it, the user is less distracted.

Most clinicians may not want Clinical Decision Support applications to interfere with their normal way of working. Any extra clicks or redundancy of information may be undesired, because it may distract them from their work. By hiding the recommendations, while providing an indication of whether recommendations are available, and optionally a number of available recommendations, the clinician can decide whether to view the recommendations, or just ignore them.

The system may comprise an explanation request unit for enabling a user to request the explanation of the reason for the determined recommendation. The system may further comprise an explanation display unit for showing the explanation to the user in response to the request. This way, the user is informed of the reason for the recommendation only when the user needs such information. This improves workflow efficiency and makes it easier for the user to verify the recommendations.

The system may comprise
a proposal input unit for enabling a user to indicate a proposed action;
a node determining unit for determining a recommendation node whose recommendation corresponds to the proposed action, the latter recommendation node being referred to hereinafter as the proposed action node;
a proposal path unit for determining a path through the decision tree that leads to the proposed action node, the latter path being referred to hereinafter as the proposed path;
a violation indicating unit for indicating to the user at least one condition of a condition node on the proposed path that is violated by the set of parameters.

The system thus created by be used to detect any mistakes or deviations from the guideline. Moreover, by providing an indication of the violated condition, the user is informed of the specific constraint that is violated by the set of parameters.

The system may comprise a divergence detector for detecting a divergence between the path determined by the path unit and the proposed path, and wherein the violation indicating unit is arranged for indicating to the user a violated condition of a condition node at the divergence. This provides a clear indication of a pertinent violated condition that is not only relevant for the proposed action, but also for the recommendation determined by the path unit.

The system may comprise a training case generator for generating a training case by selecting a set of parameters satisfying the conditions of condition nodes along a path through the decision tree to a predetermined recommendation node. This way, a training case may be generated for a specific predetermined recommendation.

The system may comprise
a difference detector for detecting a difference between two decision trees by identifying a decision node or a recommendation node in a first decision tree that has a different condition or recommendation in a corresponding node of a second decision tree or that is not present in the second decision tree;
a training path generator for generating a path through the decision tree comprising the identified decision node or recommendation node, the latter path being referred to hereinafter as training path;
wherein the training case generator is arranged for using the training path as the path to generate the training case.

This allows the system to generate automatically a training case that involves new or changed conditions in a new version of a guideline.

The system may comprise
a confirm unit for enabling a user to confirm the recommendation;
an execution unit for triggering execution or planning of the recommendation or including the recommendation into the report, in response to the confirmation by the user.

This allows the user to quickly implement a recommendation. Even when a clinician knows the guideline recommendation, she needs to document what type of treatment will be provided together with some details that are likely also described in the guidelines themselves. Recording this information costs effort and takes costly time. The confirm unit and execution unit allow an easy, for example one-click, acceptance of a recommendation (or a recommendation set). The guideline recommendation may then automatically be filled in as far as possible. In this way, the clinician does not need to manually document standard information that is already described in the guidelines.

In another aspect, the invention provides a workstation comprising a system set forth herein.

In another aspect, the invention provides a method of providing decision support, comprising
determining a determined path through a decision tree that leads to a determined recommendation node comprising a determined recommendation, wherein the decision tree comprises condition nodes and recommendation nodes, wherein a condition node comprises a condition associated with a particular branch of the decision tree, and wherein a recommendation node comprises a recommendation associated with one or more conditions of one or more condition nodes on a path towards the recommendation node, and wherein the determining comprises taking into account the conditions of the condition nodes on the path by evaluating the conditions based on a set of parameters; and
generating an explanation of a reason for the determined recommendation based on at least one of the condition nodes on the path that leads to the recommendation node.

In another aspect, the invention provides a computer program product comprising instructions for causing a processor system to perform a method set forth herein.

It will be appreciated by those skilled in the art that two or more of the above-mentioned embodiments, implementations, and/or aspects of the invention may be combined in any way deemed useful.

Modifications and variations of the workstation, the system, the method, and/or the computer program product, which correspond to the described modifications and variations of the system, can be carried out by a person skilled in the art on the basis of the present description.

BRIEF DESCRIPTION OF THE DRAWINGS

These and other aspects of the invention are apparent from and will be elucidated hereinafter with reference to the drawings. The drawings are diagrammatic and may not be drawn to scale. Throughout the figures, similar items have been indicated by means of the same reference numerals.

DETAILED DESCRIPTION OF EMBODIMENTS

Figure 1:
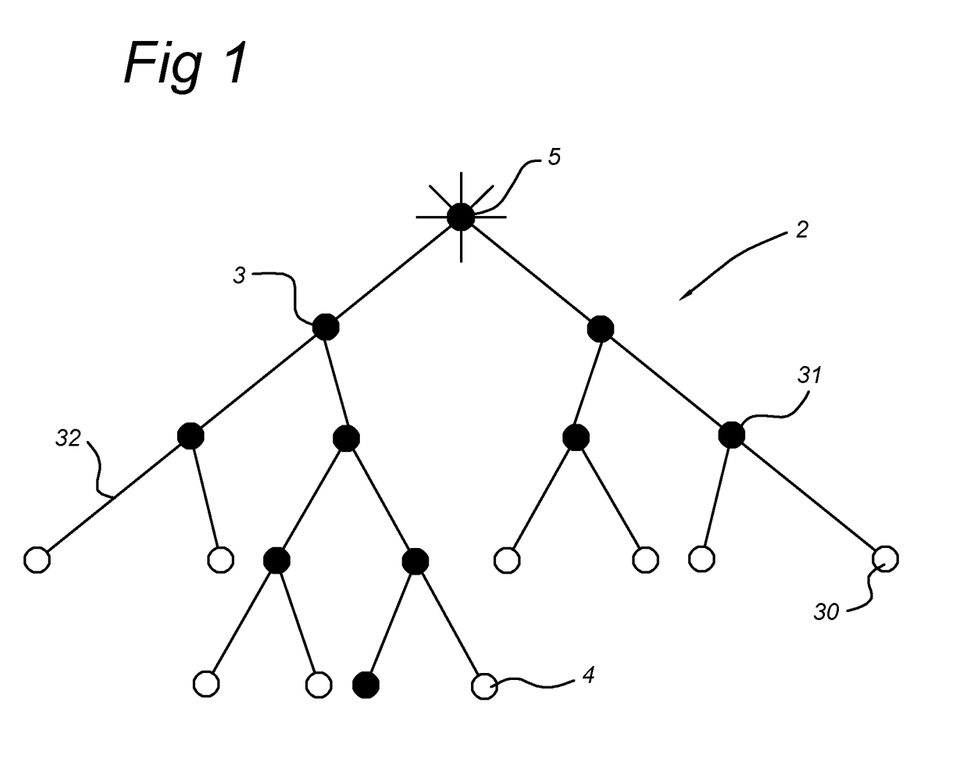
FIG. 1 is a sketch of a decision tree.

FIG. 1 illustrates a decision tree 2. The decision tree has a root node 5 which may act as a starting point for a path through the decision tree. Condition nodes 3, drawn as solid dots, are nodes of the decision tree that have a condition associated with them. The recommendation nodes 4, drawn as circles, are the leaf nodes of the tree. Edges connect the different kinds of nodes, to indicate possible routes along the nodes that a path may follow. The decision tree may be modeled as a graph structure and stored in a computer memory.

Figure 2:
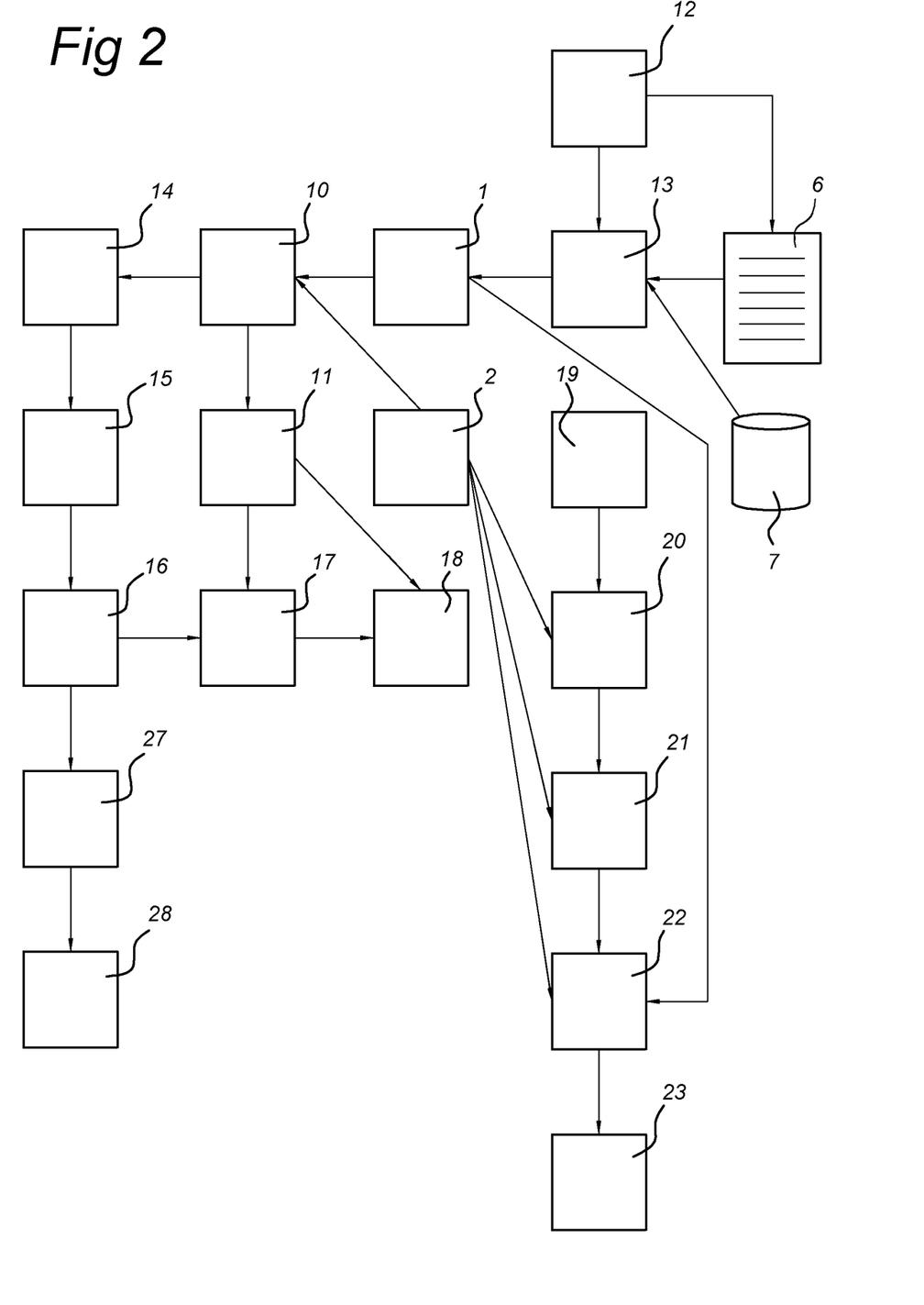
FIG. 2 is a block diagram showing aspects of a decision support system.

FIG. 2 illustrates a system for decision support. The system may be implemented on a computer system, such as a standalone computer or workstation, a distributed computer system, or a handheld device. The system may also be implemented using dedicated electronic circuitry. The system may comprise user input device, such as a touch sensitive screen, a mouse pointer, and/or a keyboard, to enable a user to operate the system. The system may further comprise a microphone for voice input, in association with a voice recognition subsystem. The system may further comprise a display for visual output and/or a loudspeaker for audio output, such as voice output. The system may further comprise a network communication interface for communicating with external data sources by means of a network connection.

The system may comprise a path unit 10 arranged for determining a path through a decision tree 2. This path may be referred to hereinafter as a determined path. The path unit 10 is arranged for determining a path that leads to a recommendation node 4. This recommendation node 4 to which the path leads is referred to hereinafter as the determined recommendation node. The recommendation nodes 4 of the decision tree 2 may comprise a recommendation. Typically the decision tree 2 may be represented in a memory, wherein the nodes 5,3,4 are represented by means of data structures, wherein the data structure of a recommendation node 4 may comprise a representation of a recommendation. Moreover, the data structures may contain identifications, such as pointers or indices, of other nodes to which they are connected by means of an edge 32 of the decision tree 2.

The decision tree 2 may comprise condition nodes 3 and recommendation nodes 4. Each condition node 3 may comprise a condition associated with a particular branch of the decision tree 2. Each recommendation node 4 may comprise a recommendation associated with the one or more conditions of the one or more condition nodes 3 on a path towards the recommendation node 4. The path unit 10 may be arranged for taking into account the conditions of the condition nodes 3 along the path by applying the conditions to a set of parameters 1. This way, the path is determined based on the conditions of the condition nodes 3, and the set of parameters 1.

The system may further comprise an explanation unit 11 arranged for generating an explanation of a reason for the determined recommendation. This reason may be generated based on at least one of the condition nodes 3 on the path that leads to the recommendation node 4. For example, when the determined path is only possible because a condition on a particular condition node 3 on the determined path is met by the set of parameters 1, then this may give rise to a "reason". Such a reason may be generated as a representation of the condition, including possibly relevant parameters of the set of parameters, in a form that can be easily understood by a user of the system. The system may be arranged for displaying the explanation automatically, or pro-actively, for example in combination with the recommendation. Alternatively, the explanation is only shown to the user upon request, as will be described hereinafter.

The path unit 10 may be arranged for determining the determined path through the decision tree 2 from a root node 5 to the determined recommendation node 4. The same root node 5 may be the starting point for all valid paths. Alternatively, a plurality of starting nodes may be used, wherein the path unit 10 may be arranged for attempting to determine valid paths from each of the starting nodes, for example.

One example of a structure for a decision tree is a structure in which a condition node 3 comprises a condition that determines whether the path is allowed to intersect the condition node 3. This structure allows the existence of a plurality of valid paths, because starting from any particular node, the conditions associated with more than one child condition node may be met by the set of parameters 1. Accordingly, the path unit 10 may be arranged for identifying a plurality of paths leading to a plurality of corresponding recommendation nodes 4, taking into account the conditions of the condition nodes 3 on the plurality of paths.

Another example of a structure for a decision tree is a structure in which a condition node 3 comprises a condition that determines which one of a plurality of child nodes will be the following node in the path. In such a case, only one path can be validly found.

The system may comprise a report unit 12 arranged for enabling a user to create a report 6. Such a report unit may provide functionality for creating a report that is known in the art per se, including functional connections to an existing healthcare information system. For example, editor operations and/or dictation with automatic speech recognition may be supported by the report unit.

The system may comprise a parameter unit 13 arranged for determining the set of parameters based on information in the report 6. The parameter unit 13 may be arranged for updating the set of parameters as the user adds more content to the report 6. For example, natural language processing may be used to extract information relevant to the set of parameters 12. Alternatively, the user may be enabled to provide the information of the report in a structured way, using e.g. computerized forms. The parameter unit 13 may, additionally or alternatively, be arranged to extract the information relevant to the set of parameters 1 from information in an information record 7. Such an information record 7 may be provided by a healthcare information system and/or a picture archiving and communication system. The parameter unit 13 may be arranged for updating automatically the set of parameters 1 when the information in the respective information record 7 is updated.

The system may comprise a presence unit 14 arranged for indicating the presence of a determined recommendation to the user. The presence unit may be operatively coupled to the parameter unit 13 and the path unit 10 in such a way that, when the set of parameters 1 is updated by the parameter unit 13, the path unit 10 is activated to update the determined path(s), and when the determined path(s) are updated, also the indication of presence of a determined recommendation is updated accordingly. For example, the presence unit 14 may be arranged for providing the indication through a user interface element that is integrated with the report unit 12.

The system may comprise a recommendation request unit 15 arranged for enabling a user to provide an indication of a request. Such request may be indicated by means of any known user input device, such as a mouse command or a keyboard.

The system may comprise a recommendation display unit 16 arranged for displaying the determined recommendation to the user in response to the request. This way, when a recommendation is present, only the indication thereof is provided to the user automatically. Only after the user indicates a request, the contents of the recommendation is provided to the user.

The system may comprise an explanation request unit 17 arranged for enabling a user to request the explanation of the reason for the determined recommendation. The explanation request unit 17 may be operatively coupled to an explanation display unit 18 that is arranged for showing the explanation to the user in response to the request. The explanation may be shown, for example in text form or graphically, or by reading out loud the reason using text-to-speech processing.

The system may comprise a proposal input unit 19 arranged for enabling a user to indicate a proposed action. Such indication may be given through an electronic form, for example. Alternatively, the user provides the indication through natural language, for example in the report. Natural language processing may be used to extract the proposed action.

The system may comprise a node determining unit 20 arranged for determining a recommendation node 30 whose recommendation corresponds to the proposed action. The latter recommendation node 30 may be referred to hereinafter as the proposed action node 30. This may be done by an expression matching algorithm, for example. An ontology comprising concepts representing aspects of recommendations and actions may be used to match actions to related recommendations.

The system may comprise a proposal path unit 21 arranged for determining a path through the decision tree 2 that leads to the proposed action node 30. The latter path may be referred to hereinafter as the proposed path. For example, the proposal path unit 21 may be arranged for determining a path, from the root node 5 to the proposed action node 30, using for example a shortest path algorithm.

The system may comprise a violation indicating unit 23 arranged for indicating to the user at least one condition of a condition node 31 on the proposed path that is violated by the set of parameters 1. This may be done by evaluating one by one the conditions on the proposed path against the set of parameters 1. When a violated condition has been detected, a representation in natural language or in another human-friendly form may be generated.

The system may comprise a divergence detector 22 arranged for detecting a divergence between the path determined by the path unit 10 and the proposed path. The violation indicating unit 23 may be arranged for indicating to the user a violated condition of a condition node 31 at the divergence. This way, the most convincing reason may be identified, because the conditions further down the proposed path may sometimes not be decisive for the error.

The system may comprise a confirm unit 27 arranged for enabling a user to confirm the recommendation. This unit may be implemented by means of a user interface element.

The system may comprise an execution unit 28 arranged for triggering execution or planning of the recommendation or including the recommendation into the report 6, in response to the confirmation by the user. This execution unit 28 may be implemented in many ways, depending on the systems with which the decision support system is connected. A connection to a planning tool could be provided that automatically finds and reserves an available time slot for performing a recommended action. A lab order may be issued. The system could be connected to some patient treatment equipment, such as respiration equipment, to influence respiration. The execution unit 28 may also be arranged for including the description of the recommended action in the report 6.

Figure 3:
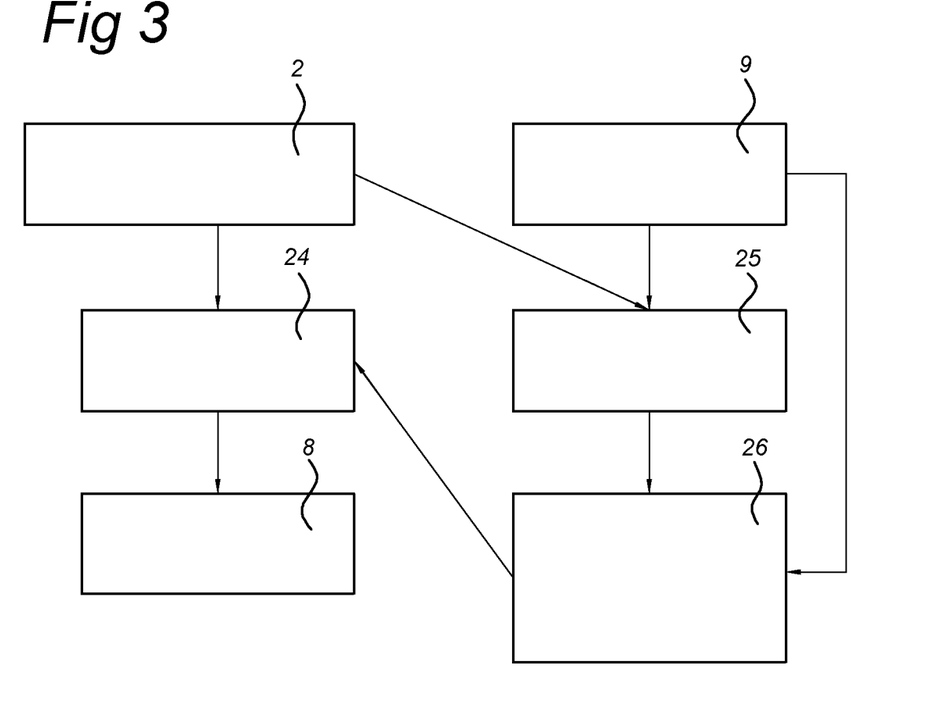
FIG. 3 is a block diagram showing aspects of a training case generator.

FIG. 2 illustrates some aspects of the system that may be implemented independently or in addition to the features described hereinabove. These aspects are related to training case generation. To this end, the system may comprise a training case generator 24. The training case generator 24 may be arranged for receiving an indication of a recommendation node 4 and/or a path through the decision tree to the recommendation node 4. This path may also be generated automatically, for example using the proposal path unit. The training case generator 24 may be arranged for generating a training case by selecting a set of parameters 8 satisfying the conditions of condition nodes along a path through the decision tree 2 to a predetermined recommendation node 4. The training case generator 24 may further comprise a natural language generator for translating the set of parameters 8 into a description of a patient case.

The system may comprise a difference detector 25 arranged for receiving two decision trees, a first decision tree 2 and a second decision tree 9. These trees can be generated manually or automatically by an external system based on two versions of a guideline. The difference detector 25 may be arranged for detecting a difference between the two decision trees 2, 9 by identifying a decision node 3 or a recommendation node 4 in the first decision tree 2 that has a different condition or recommendation in a corresponding node of the second decision tree 9 or that is not present in the second decision tree 9. Consequently, a condition that is applied differently in both versions of the guideline is identified. The system can generate a training case that forces a student to evaluate this condition.

To this end, the system may comprise a training path generator 26 arranged for generating a path through the decision tree 9 comprising the identified decision node or recommendation node. The latter path may be referred to hereinafter as training path. The training case generator 24 may be arranged for using the training path as the path to generate the training case.

Figure 4:
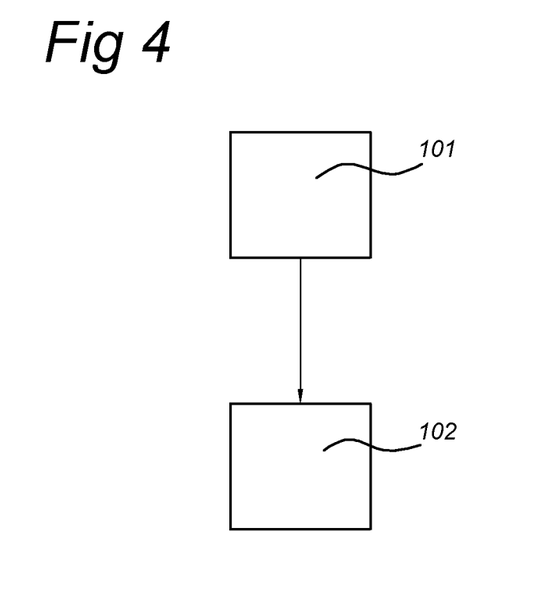
FIG. 4 is a flowchart of a decision support method.

FIG. 4 shows a flowchart of a method of providing decision support. The method may comprise step 101 of determining a path through a decision tree that leads to a determined recommendation node comprising a determined recommendation, wherein the decision tree comprises condition nodes and recommendation nodes, wherein a condition node comprises a condition associated with a particular branch of the decision tree, and wherein a recommendation node comprises a recommendation associated with the one or more conditions of the one or more condition nodes on a path towards the recommendation node, and wherein the path unit is arranged for taking into account the conditions of the condition nodes along the path by applying the conditions to a set of parameters.

The method may further comprise step 102 of generating an explanation of a reason for the determined recommendation based on at least one of the condition nodes on the path that leads to the recommendation node.

The method may be extended and/or modified based on the functionality disclosed in this description. The method may be implemented by means of a computer program.

The decision support system may comprise the following elements:
- Decision support user interface (UI): the user interface based on the elements to provide guideline-based decision support.
- Decision-tree formalism: a formalism to model guideline-based knowledge as a decision tree.
- Recommendation algorithm: an algorithm to traverse a decision-tree to find guideline recommendations.
- Recommendation explanation algorithm: an algorithm to provide an explanation for a given recommendation.
- Recommendation metadata: metadata from a recommendation in a decision tree to automatically perform an action that would otherwise need to be performed by the user.

A decision tree is a tree-based data structure, of which a node N in the tree may be one of the following types:
- A decision node represents a node containing a condition, for example a statement that can be either true, false, or unknown (which usually is converted to false). The node has a textual description of the decision it represents. Furthermore it contains a formal rule that takes as input a set of patient characteristics and as output gives whether this condition holds given those characteristics. Each decision node may have a set of child nodes, and in this way spans a decision tree. For example, formally stated, for decision node N:
  description: N.Description→String
  rule: N.Rule(p1, p2, . . . )→{True,False,Unknown}
  children: N.Children→Set {Node}
- A recommendation node represents a node that describes a treatment recommendation from a guideline. Next to the text-based recommendation, the node can contain metadata for specific treatments (e.g. chemotherapy protocols) or links to documents (the originating guidelines) for better integration into a clinical application. For example, formally, for a recommendation node N:
  recommendation description: N.Recommendation String
  recommendation metadata: N.RecommendationData Set {Data}

Figure 5:
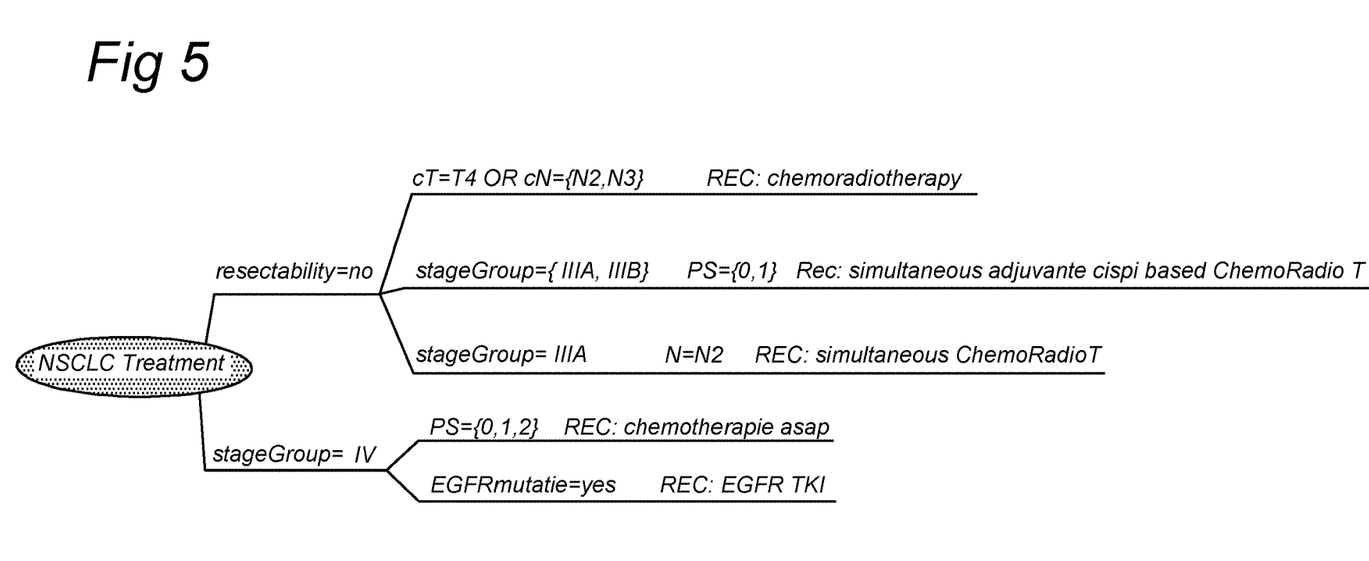
FIG. 5 is a diagram of a decision tree.

FIG. 5 graphically shows an example of a clinical decision tree based on Lung Cancer guidelines. Each item denoted with text in the tree represents a node. Items that start with "REC" are recommendation nodes, other items are decision nodes. For example, the node "resectability=no" should evaluate to true if the patient has an unresectable tumor. Otherwise it should evaluate to false. The "REC: chemoradiotherapy" node may have additional metadata attached to it representing the clinical protocol, dosage, etc. that is recommended by the guideline. Optionally, it also has metadata referring to the original guideline document and/or other supporting clinical sources, such as clinical trial results or papers that describe this recommendation.

The recommendation algorithm may use an instance of the decision-tree formalism to find recommendations that are reachable for a certain set of input data (or parameters 1). The algorithm may operate according to the following steps:
  The algorithm starts out with an empty Recommendation set.
  The algorithm receives a Node N (initially the root of the decision tree) and a set of patient data Set{PD} (age, gender, disease characteristics, etc) as input.

If N is a Decision Node, it performs the following actions:
  The algorithm evaluates N.Rule(Set{PD}), that is the rule associated with the node given the input patient data.
  If the rule evaluates to True, the algorithm will recursively traverse each Node in N.Children. These are all the child nodes of the current node.
  If the rule evaluates to False, the algorithm will end the current traversal, meaning that no recommendations on this path will be added.
  In this way, all reachable paths with true rules will be traversed.
If N is a Recommendation Node, then the algorithm adds the recommendation N.Recommendation text belonging to the node to the Recommendation set.
Finally, the algorithm returns the set of recommendations. These are all the recommendations for which all preconditions are true, and therefore hold for the entered patient data.

In the example of FIG. 5, if given the following input data:
resectability=no
stagegroup=IIIA
N=N2,
then the recommendation "REC: simultaneous ChemoRadioT" would be the only possible recommendation.

The recommendation explanation algorithm may calculate a path from a recommendation node, which is usually a leaf of the decision tree, back to the root of the decision tree. The algorithm may operate as follows:
  The algorithm starts with an empty set of Explanations.
  The algorithm receives a Node N as input (usually a recommendation node).
  The algorithm adds the N.Description, a description of the node, to the set of Explanations.
  While the node's parent, P=N.Parent, exists (indicating that it is not the root node), the algorithm adds P.Description to the explanation set.
  Finally, when there is no N.Parent, the algorithm returns the set of Explanations.

The set of explanations functions as the explanation, or reason why a certain recommendation is given.

In the example of FIG. 5, if the input is the recommendation node "REC: simultaneous ChemoRadioT", then the explanation would be:
resectability=no
stagegroup=IIIA
N=N2.

In the decision tree, Recommendation Nodes may have associated structured metadata, N.RecommendationData, representing structural information from the guideline. For example, the recommendation node "REC: simultaneous ChemoRadioT" could have the following metadata:
Treatment type: ChemoRadiotherapy
Protocol: Cisplatin
Dose: 4×40 mg.

When the clinician chooses this recommendation, this structured information can be used by the decision support application to perform automatic filling in of information, as was shown in the Decision support UI. This can significantly save valuable time and prevent errors.

The Virtual case generator (or training case generator 24) may contain an implementation of an algorithm to take a recommendation of a decision tree as input, and creates a virtual patient case based on the rules defined in the tree that would end up in the specified recommendation.

For example, in FIG. 5, if the input would be the recommendation node named "REC: chemotherapy", then the algorithm would evaluate the rule before the node, being "cT=T4 OR cN={N2,N3}" (the curly brackets denote a set of possible values). The algorithm examines the possible inputs for the rule to become true. For this example rule, the possible values are cT=T4, cN=N2, or cN=N3. The algorithm may then choose one of these possibilities. Then, the algorithm recursively does the same for the parent node. In this case, there is only one option for the rule "respectability=no". The result of this process is a "virtual patient case", or a training case, describing a patient having a certain condition, for which the recommendation is the recommendation that was received as input.

One possible virtual case for the example figure is:
Resectability=no
cN=N2

The training user interface may provide a user interface that presents virtual patient cases to the user, along with a number of possible guideline recommendations. These recommendations may contain the recommendation that was used to generate the virtual case, which would be the recommendation that is the correct answer. The user interface may randomly also choose a number of alternative recommendations which are not correct. The resulting list of options may be then shown to the user to generate a multiple choice question. Alternatively, an open question may be generated.

An example of how the application could present the virtual case, with the previous example based on FIG. 5, along with some alternative treatment recommendation is as follows:

"A patient with NSCLC has the following characteristics:
Resectability=no
cN=N2
What is the recommended treatment?
A) simultaneous ChemoRadioTherapy
B) EGFR TKI
C) chemotherapy asap".

The user may choose one of the offered treatments A, B, or C, upon which the user interface may display whether the choice is correct or not. If the user was not correct, the application can display the graphical decision tree, or a derivative thereof, showing the path leading to the incorrect answer chosen by the user, and the path leading to the correct answer. This gives direct insight into why the chosen treatment is incorrect. Optionally, the application also provides links to the relevant sections in the original guideline document where the correct treatment is described in full detail.

The delta analyzer module, or difference detector 25, is an optional module that can analyze different versions of a clinical guideline and identify the changes from one version to the next. This is useful for training, when the focus of the training is on updating existing knowledge. The way the delta analyzer operates may be as follows:

It receives two versions of the same computer interpretable guideline (CIG) as input: C'old and C'new, in form of decision trees.

It traverses both decision trees simultaneously from the root towards the leafs.

As long as the nodes in C'old and C'new are the same, nothing happens.

If, at a certain position, the current node in C'old and C'new are different, the algorithm will mark the node at this position as changed. It may be arranged for not further traversing the subtrees from this node, since these are likely to differ.

When all paths have been traversed, it may return the marked set of changed nodes.

The result of the delta analyzer can serve as an extra input for the virtual case generator, or training case generator 24. This generator can then use this input to focus the virtual case generation process on the parts of the guideline that have changed. This is especially useful for training users that already have good basic knowledge of the guidelines, but require training for updated versions of the guidelines.

The following provides an example application of a decision tree. The example is a real-world example based on the clinical guidelines for Non Small Cell Lung Cancer (NSCLC).

Figure 6:
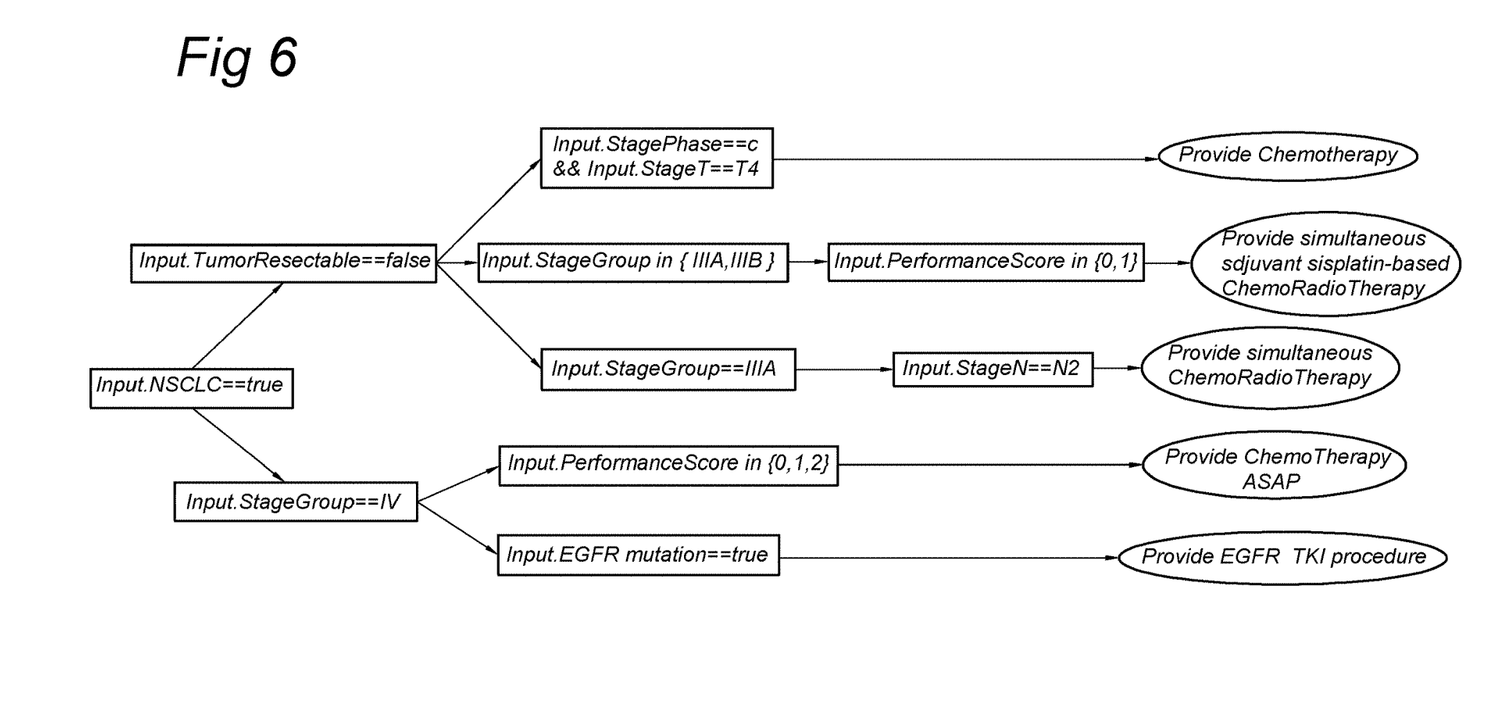
FIG. 6 is a diagram of a decision tree.

FIG. 6 shows a decision tree that was derived manually from the guidelines. It comprises square nodes (such as the node labeled "Input.TumorResectablefalse") that represent predicates about the input data that result in either true or false, and oval nodes (such as the node labeled "Provide Chemotherapy") that represent a potential output of the algorithm. These potential outputs are the clinical recommendations that can be given based on the guidelines. The node labeled "Input.NSCLCtrue" is the root node of the decision tree.

The example decision tree expects the following input data, which should be derived from the available patient data in a system (for example an EMR):
Input.NSCLC→{true,false}
Input.TumorResectable→{true,false}
Input.StagePhase→{c,p}
Input. StageT→{T1,T2,T3,T4}
Input.StageGroup→{I,II,IIIA,IIIB,IV}
Input.PerformanceScore→{0 . . . 10}
Input. StageN→{N0,N1,N2}
Input.EFGRmutation→{true,false}

The output of the algorithm is a list of recommendations (the text in the rounded nodes).

Based on the parameters for a patient, the algorithm evaluates, from left to right, each square node, and proceeds to the right as long as the predicates result in "true", otherwise the algorithm continues the search in other branches of the tree. When the algorithm reaches one of the round nodes, this means that a clinical recommendation can be given. Because it may be the case that multiple recommendations can be given at the same time (see FIG. 9), the algorithm may continue with the other branches.

Figure 7:
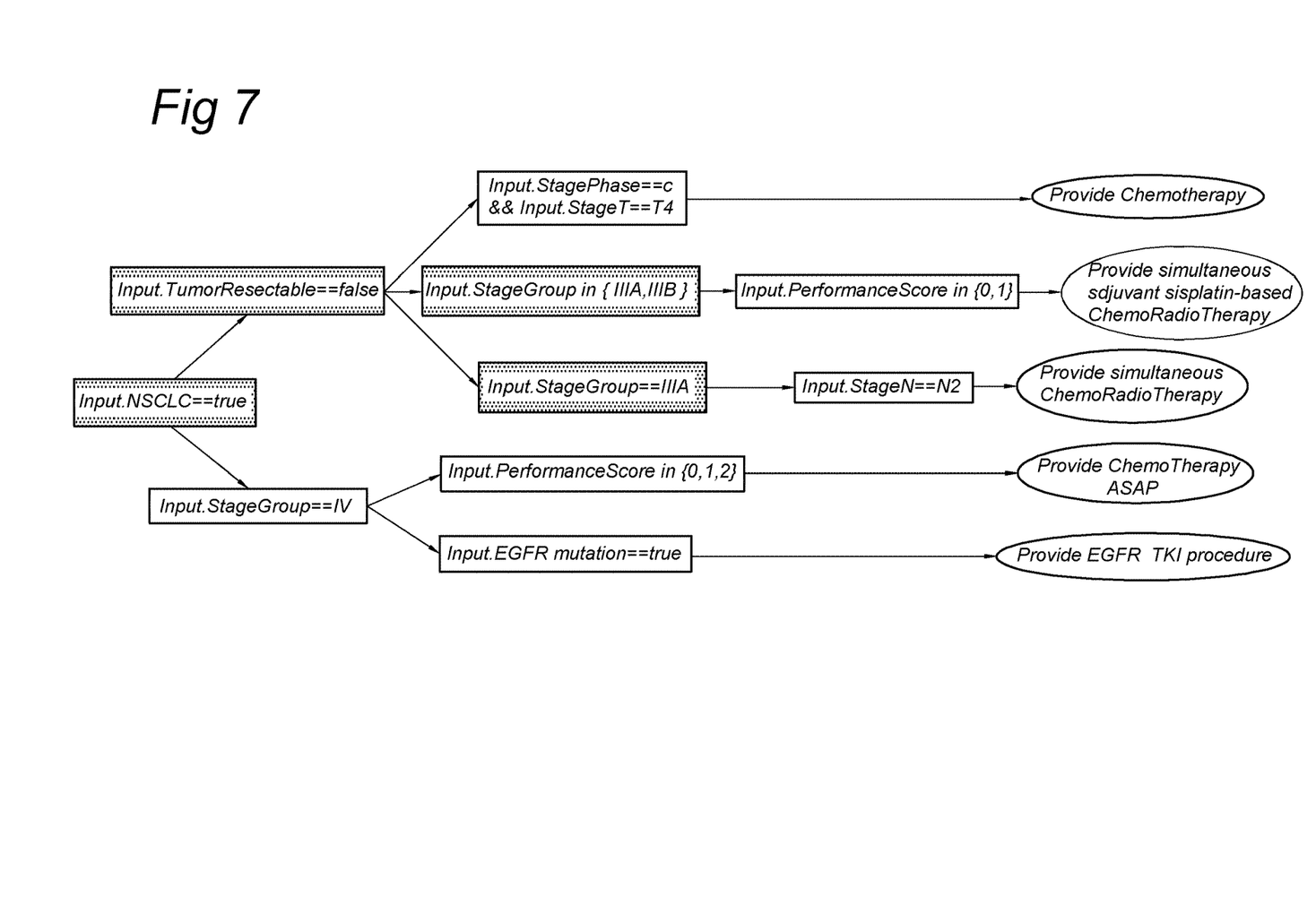
FIG. 7 is a diagram of a decision tree applied to a set of parameters.

FIG. 7 shows an example of the algorithm processing the following input parameters:
Input.NSCLC=true
Input.TumorResectable=false
Input.StageGroup=IIIA In FIGS. 7 to 9, the nodes that have a gray background evaluate to "true". For example, in FIG. 7, the node labeled "Input.TumorResectablefalse" has a gray background and evaluates to "true". What can be seen is that, though some of the nodes are activated, no recommendation nodes are reached, so there are no recommendations that can be given. Thus, the algorithm ends and returns an empty set of recommendations.

Figure 8:
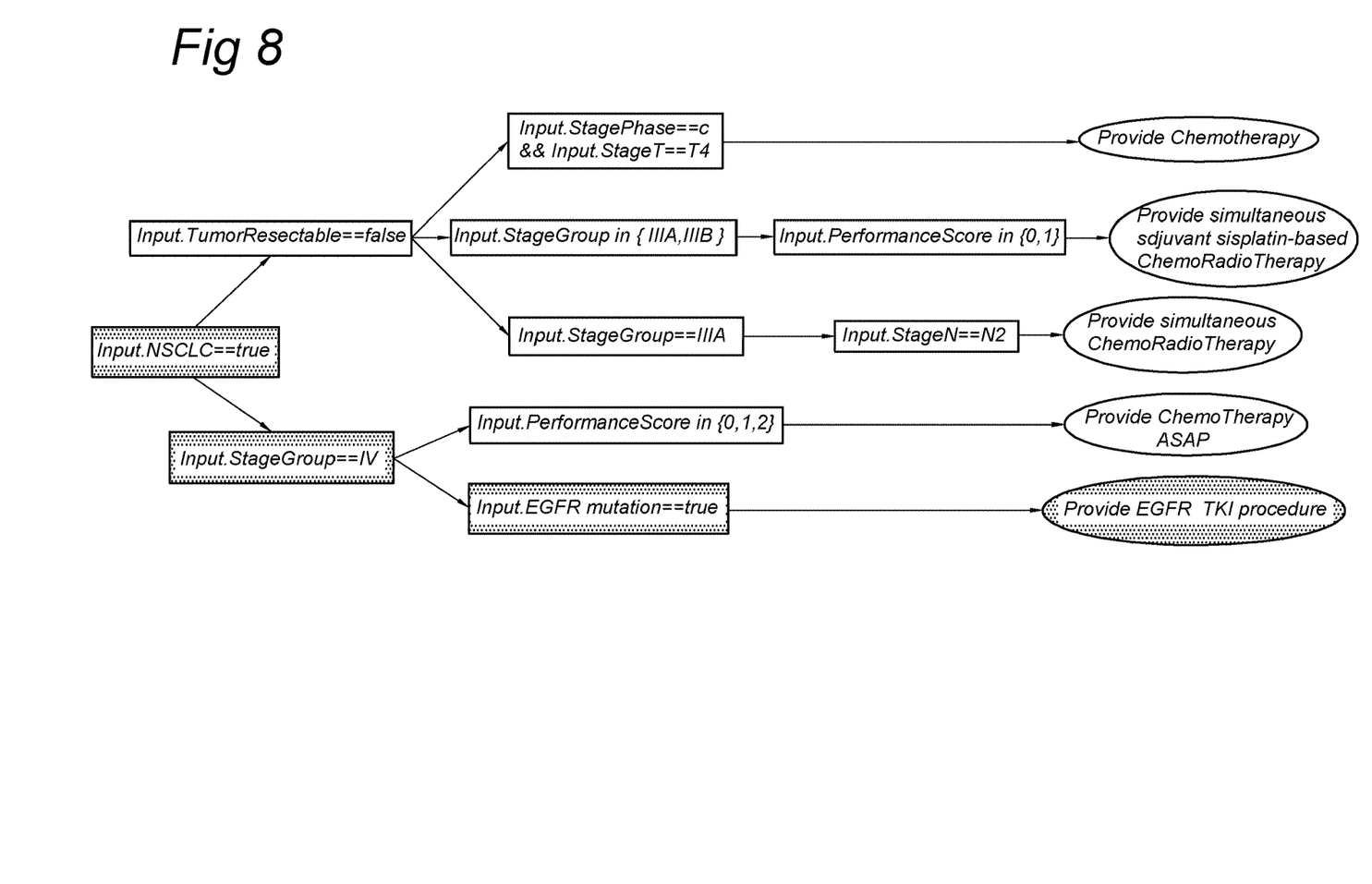
FIG. 8 is a diagram of a decision tree applied to a set of parameters.

FIG. 8 shows the situation based on the following input parameters:
Input.NSCLC=true
Input.StageGroup=IV
Input.PerformanceScore=1

Based on this input exactly one recommendation, labeled "Provide Chemo Therapy ASAP", becomes active. This is the clinical recommendation that can be given to the user based on the input data.

Figure 9:
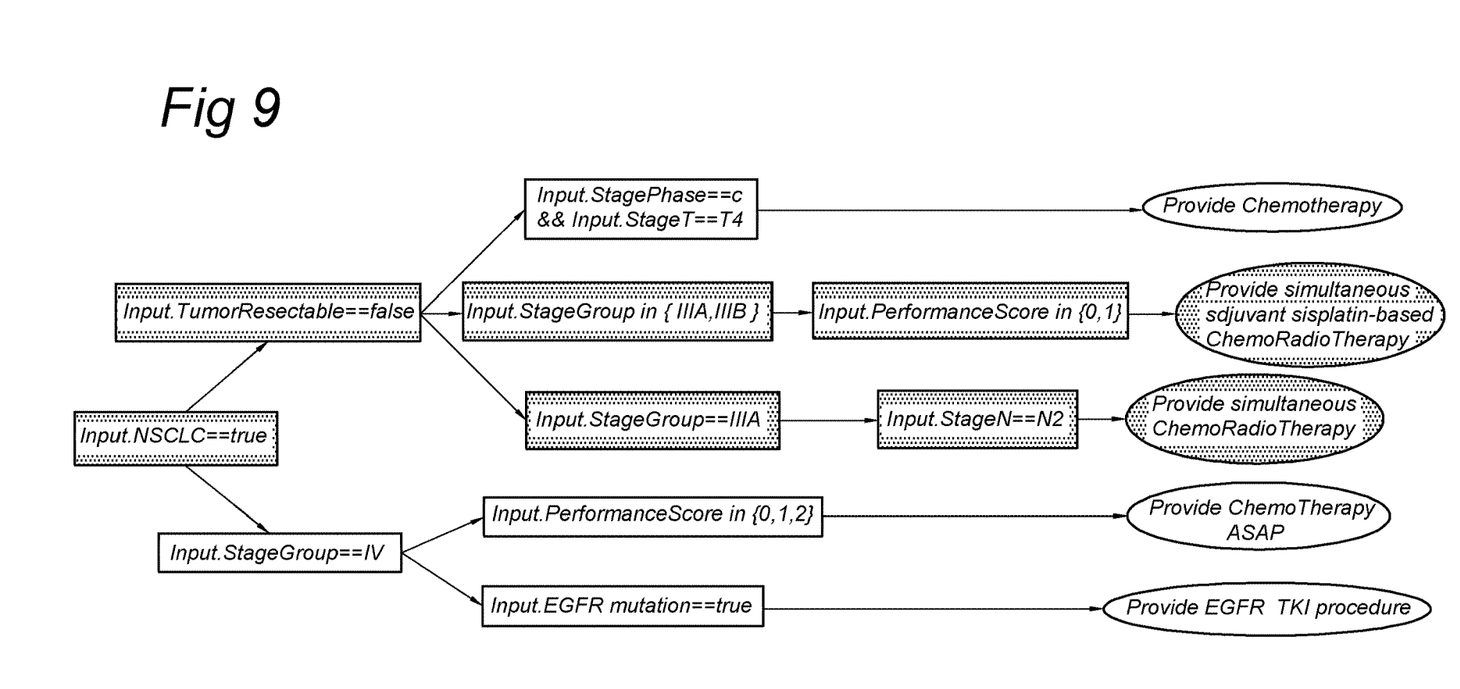
FIG. 9 is a diagram of a decision tree applied to a set of parameters.

FIG. 9 shows a situation based on the following input data:
Input.NSCLC=true
Input.TumorResectable=false
Input.StageGroup=IIIA
Input.PerformanceScore=1
Input. StageN=N2

In this example, multiple recommendations become active at the same time. In particular, the recommendations "Provide simultaneous adjuvant cisplatin-based ChemoRadioTherapy" and "Provide simultaneous ChemoRadioTherapy" are active. The algorithm thus returns both the recommendations, such that the user can select the most appropriate one.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a flash drive or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A method of providing decision support, comprising:
   modeling, by a processor, a clinical guideline as a decision tree, the decision tree comprising a root node, condition nodes and recommendation nodes, wherein the root node comprises a starting point for determining a path through the decision tree via at least one of the condition nodes to at least one of the recommendation nodes, the condition nodes each comprise a condition determining whether the path is allowed to intersect the condition node, and the recommendation nodes each comprise a treatment recommendation adhering to the clinical guideline;
   evaluating, by the processor, the conditions of the condition nodes in view of a set of patient parameters;
   determining, by the processor, the path through the decision tree to the at least one recommendation node, the at least one recommendation node comprising a determined recommendation, wherein the condition nodes are activated or deactivated based on whether the condition is met in view of the patient parameters, wherein the path is allowed to intersect with the activated condition nodes;
   generating, by the processor, an explanation of a reason for the determined recommendation based on at least one of the condition nodes on the path that leads to the recommendation node;
   receiving, by the processor via a user interface, a proposed treatment action from a user;
   determining, by the processor, a recommendation node whose recommendation corresponds to the proposed treatment action, the latter recommendation node being referred to hereinafter as the proposed action node;
   determining, by the processor, a path through the decision tree that leads to the proposed action node, the latter path being referred to hereinafter as the proposed path;
   comparing, by the processor, the path determined by the processor and the proposed path to detect a divergence between the path determined by the processor and the proposed path; and
   indicating, by the processor via the user interface, to the user a violated condition of a condition node at the divergence.

2. The method of claim 1, further comprising:
   determining, by the processor, the determined path through the decision tree from a root node to the determined recommendation node.

3. The method of claim 1, wherein a condition node comprises a condition that determines whether the path is allowed to intersect the condition node.

4. The method of claim 1, further comprising:
identifying, by the processor, a plurality of paths leading to a plurality of corresponding recommendation nodes, taking into account the conditions of the condition nodes on the plurality of paths.

5. The method of claim 1, further comprising:
enabling a user, by the processor via the user interface, to create a report; and
determining, by the processor, the set of parameters based on information in the report and/or information in an information record.

6. The method of claim 1, further comprising:
indicating, by the processor via the user interface, the presence of a determined recommendation to the user;
enabling a user, by the processor via the user interface, to provide an indication of a request; and
displaying, by the processor via the user interface, the determined recommendation to the user in response to the request.

7. The method of claim 1, further comprising:
enabling a user, by the processor via the user interface, to request the explanation of the reason for the determined recommendation; and
showing, by the processor via the user interface, the explanation to the user in response to the request.

8. The method of claim 1, further comprising:
enabling a user, by the processor via the user interface, to confirm the recommendation; and
triggering, by the processor, execution or planning of the recommendation or including the recommendation into the report, in response to the confirmation by the user.

9. The method of claim 1, further comprising:
generating, by the processor, a training case by selecting a set of parameters satisfying the conditions of condition nodes along a path through the decision tree to a predetermined recommendation node.

10. The method of claim 9, further comprising:
detecting, by the processor, a difference between two decision trees by identifying a decision node or a recommendation node in a first decision tree that has a different condition or recommendation in a corresponding node of a second decision tree or that is not present in the second decision tree;
generating, by the processor, a path through the decision tree comprising the identified decision node or recommendation node, the latter path being referred to hereinafter as training path;
wherein generating the training case comprises using the training path as the path to generate the training case.

11. A non-transitory computer readable medium comprising instructions for causing a processor system to perform a method for providing decision support, the method comprising:
modeling a clinical guideline as a decision tree, the decision tree comprising a root node, condition nodes and recommendation nodes, wherein the root node comprises a starting point for determining a path through the decision tree via at least one of the condition nodes to at least one of the recommendation nodes, the condition nodes each comprise a condition determining whether the path is allowed to intersect the condition node, and the recommendation nodes each comprise a treatment recommendation adhering to the clinical guideline;
evaluating the conditions of the condition nodes in view of a set of patient parameters;
determining the path through the decision tree to the at least one recommendation node, the at least one recommendation node comprising a determined recommendation, wherein the condition nodes are activated or deactivated based on whether the condition is met in view of the patient parameters, wherein the path is allowed to intersect with the activated condition nodes;
generating an explanation of a reason for the determined recommendation based on at least one of the condition nodes on the path that leads to the recommendation node;
receiving, via a user interface, a proposed treatment action from a user;
determining a recommendation node whose recommendation corresponds to the proposed treatment action, the latter recommendation node being referred to hereinafter as the proposed action node;
determining a path through the decision tree that leads to the proposed action node, the latter path being referred to hereinafter as the proposed path;
comparing the path and the proposed path to detect a divergence between the path and the proposed path; and
indicating, via the user interface, to the user a violated condition of a condition node at the divergence.

* * * * *